United States Patent
Maszara et al.

(10) Patent No.: US 7,078,299 B2
(45) Date of Patent: Jul. 18, 2006

(54) FORMATION OF FINFET USING A SIDEWALL EPITAXIAL LAYER

(75) Inventors: Witold P. Maszara, Morgan Hill, CA (US); Jung-Suk Goo, Stanford, CA (US); James N. Pan, Fishkill, NY (US); Qi Xiang, San Jose, CA (US)

(73) Assignee: Advanced Micro Devices, Inc., Austi, TX (US)

( * ) Notice: Subject to any disclaimer, the term of this patent is extended or adjusted under 35 U.S.C. 154(b) by 0 days.

(21) Appl. No.: 10/654,631

(22) Filed: Sep. 3, 2003

(65) Prior Publication Data

US 2005/0048727 A1    Mar. 3, 2005

(51) Int. Cl.
*H01L 21/336* (2006.01)

(52) U.S. Cl. ............... 438/285; 438/933; 257/E21.562

(58) Field of Classification Search ............ 438/149, 438/197, 285, 933, 585, 590; 257/E21.562, 257/E21.571
See application file for complete search history.

(56) References Cited

U.S. PATENT DOCUMENTS

| | | | |
|---|---|---|---|
| 6,689,650 B1 * | 2/2004 | Gambino et al. ........... 438/157 |
| 6,777,288 B1 * | 8/2004 | Padmanabhan et al. ..... 438/250 |
| 6,815,738 B1 * | 11/2004 | Rim ........................... 257/256 |
| 6,936,516 B1 * | 8/2005 | Goo et al. ................... 438/283 |
| 6,943,087 B1 * | 9/2005 | Xiang et al. ................ 438/311 |
| 6,949,421 B1 * | 9/2005 | Padmanabhan et al. ..... 438/156 |
| 2004/0253792 A1* | 12/2004 | Cohen et al. ............... 438/400 |
| 2005/0205932 A1* | 9/2005 | Cohen ........................ 257/347 |

* cited by examiner

*Primary Examiner*—Michael Lebentritt
*Assistant Examiner*—Stanetta Isaac
(74) *Attorney, Agent, or Firm*—Foley & Lardner, LLP

(57) ABSTRACT

A method of forming a finFET transistor using a sidewall epitaxial layer includes forming a silicon germanium (SiGe) layer above an oxide layer above a substrate, forming a cap layer above the SiGe layer, removing portions of the SiGe layer and the cap layer to form a feature, forming sidewalls along lateral walls of the feature, and removing the feature.

11 Claims, 4 Drawing Sheets

FORMATION OF FINFET USING A SIDEWALL EPITAXIAL LAYER

FIELD OF THE INVENTION

The present invention is related to integrated circuit (IC) devices. More particularly, the present invention relates to a method of forming a strained silicon FIN FET using a sidewall epitaxial layer.

BACKGROUND OF THE INVENTION

Metal-Oxide-Semiconductor Field Effect Transistor (MOSFET) technology is well known and widely used in the electronics industry. Performance enhancement between generations of devices is generally achieved by reducing the size of the device, resulting in an enhancement in device speed. This is generally referred to as device "scaling." As MOSFETs are scaled to channel lengths below 100 nm, conventional MOSFETs suffer from several problems. In particular, interactions between the source and drain of the MOSFET degrade the ability of the gate of the same to control whether the device is on or off. This phenomenon is called the "short-channel effect".

Silicon-on-insulator (SOI) MOSFETs are formed with an insulator (usually, but not limited to, silicon dioxide) below the device active region, unlike conventional "bulk" MOSFETs, which are formed directly on silicon substrates, and hence have silicon below the active region. SOI is advantageous since it reduces unwanted coupling between the source and the drain of the MOSFET through the region below the channel. This result is often achieved by ensuring that all the silicon in the MOSFET channel region can be depleted by the gate (called a fully depleted SOI MOSFET). As device size is scaled, however, this becomes increasingly difficult because the distance between the source and drain is reduced. The reduced distance increases interaction with the channel, reducing gate control and increasing short channel effects.

The double-gate MOSFET structure places a second gate in the device, such that there is a gate on either side of the channel. This allows gate control of the channel from both sides, reducing short channel effects. Additionally, when the device is turned on using both gates, two conduction ("inversion") layers are formed, allowing for more current flow or higher drive current. An extension of the double-gate concept is the "surround-gate" or "wraparound-gate" concept, where the gate is placed such that it completely or almost-completely surrounds the channel, providing better gate control.

These double-gate MOSFETs are sometimes referred to as "FinFET" structures because of their shape. One method of forming FinFET structures is by forming channels and source and drain regions by etching SOI film. Resulting channel structure carries current along both sidewalls of the fin.

In silicon MOSFET devices, it has been shown that performance can be enhanced by enhancing the mobility of electrons and holes in, the channel region. One way to enhance mobility is by the use of strained materials, such as strained silicon. A material under appropriate stress can enhance electron and/or hole carrier mobility due to modulation or material's energy band structure by the strain.

Thus, there is a need for a method of forming a strained silicon finFET. Further, there is a need for enhanced channel mobility using double-gate MOSFETs and strained materials. Even further, there is a need for improved electron mobility in the channel region.

SUMMARY OF THE INVENTION

An exemplary embodiment relates to a method of forming a strained silicon finFET using a sidewall epitaxial layer. The method includes forming a silicon germanium (SiGe) layer above an oxide layer above a substrate, forming a cap layer above the SiGe layer, removing portions of the SiGe layer and the cap layer to form a feature, epitaxially growing strained silicon sidewalls along lateral walls of the feature, and selectively removing the feature.

Another exemplary embodiment relates to a method of forming strained silicon structures. The method includes depositing a material layer above an oxide layer above a substrate, depositing a cap layer above the material layer, patterning the material layer and the cap layer to form a gate structure, forming strained silicon sidewalls along lateral walls of the gate structure, and providing a selective etch to remove the gate structure and leave the strained silicon sidewalls to define strained silicon structures.

Another exemplary embodiment relates to an integrated circuit having narrow strained silicon structures formed by a process. The process including depositing a silicon germanium (SiGe) layer above an oxide layer above a substrate, depositing a layer above the SiGe layer, selectively etching portions of the SiGe layer and the layer above the SiGe layer to expose portions of the oxide layer, growing an epitaxial layer of strained silicon on the sidewalls of remaining portions of the SiGe layer, and removing selected portions of the SiGe layer and the layer above the SiGe layer.

Other principle features and advantages of the invention will become apparent to those skilled in the art upon review of the following drawings, the detailed description, and the appended claims.

BRIEF DESCRIPTION OF THE DRAWINGS

The exemplary embodiments will hereafter be described with reference to the accompanying drawings, wherein like numerals will denote like elements, and.

DETAILED DESCRIPTION OF EXEMPLARY EMBODIMENTS

Figure 1:
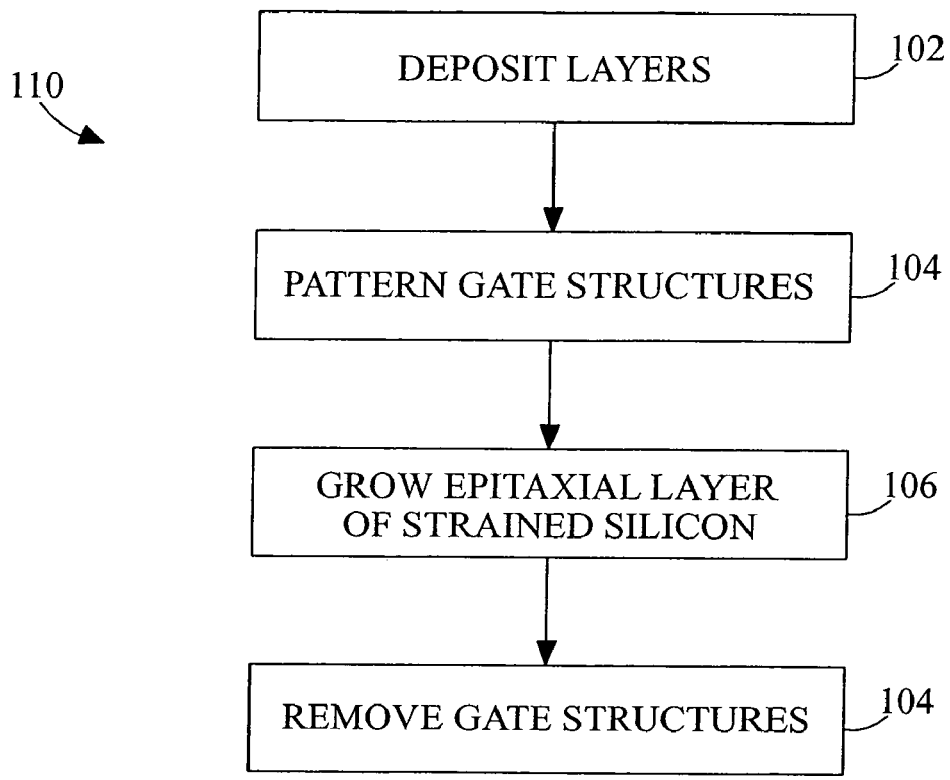
FIG. 1 is a general process flow diagram of a process of forming a strained silicon finFET using a sidewall epitaxial layer in accordance with an exemplary embodiment.

With reference to FIG. 1, an advantageous process 100 forms strained silicon finFET structures using a sidewall epitaxial layer. The strain in these finFET structures can be used to enhance electron mobility. While process 100 is described by way of example, additional, fewer, or different operations may be performed. Process 100 is not limited to the operations, materials, or techniques described herein.

In an operation 102, various layers are formed over a substrate. For example, a buried oxide layer is formed above a substrate and a silicon germanium layer (SiGe) layer is formed above the buried oxide layer. The silicon germanium (SiGe) layer can be deposited above the buried oxide layer using any of a variety of deposition techniques. A cap layer can be deposited above the silicon germanium layer.

In an operation 104, gate structures are patterned from the silicon germanium layer and cap layer provided in operation 102. Structures can be patterned from the silicon germanium layer and cap layer.

In an operation 106, an epitaxial layer of strained silicon is grown along lateral walls of the SiGe structures formed in operation 104. The strained silicon forms sidewalls that can have a width of 1 to 50 nm. In an operation 108, the gate structures are removed using a mask, leaving the sidewalls above the buried oxide layer.

Figure 2:
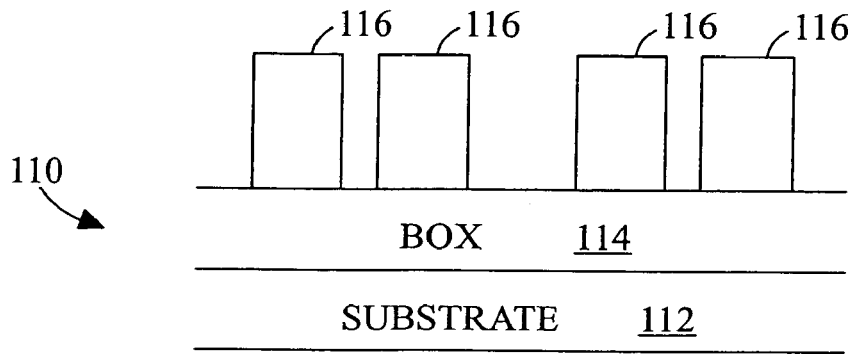
FIG. 2 is a schematic cross-sectional view of a portion of an integrated circuit including strained silicon finFET structures in accordance with an exemplary embodiment of the present invention.

With reference to FIGS. 1–9, process 100 (FIG. 1) will be described below. In FIG. 2, a portion 110 of an integrated circuit includes a substrate 112, an oxide layer 114, and fins 116. Portion 110 is preferably part of an ultra-large-scale integrated (ULSI) circuit. In an exemplary embodiment, portion 110 is manufactured as part of the integrated circuit on a semiconductor wafer (e.g., a silicon wafer). Substrate 112 can be any type of integrated circuit substrate suitable for building a circuit including strained silicon fins.

Oxide layer 114 can be a variety of different oxide materials including silicon dioxide. In one embodiment, layer 114 is a buried oxide layer of SOI wafer. Layer 114 can have any thickness typically 100–200 nm. Fins 116 are formed using strained silicon. Preferably, fins 116 are epitaxial layers of strained silicon. As understood by a person of skill in the art, epitaxial growth refers to the growth of the crystals of one crystalline material on the crystal face of another material such that the crystalline substrates of both materials have the same structural orientation. Fins 116 can have a width of 1–50 nm and a height approximately that of SiGe layer 118.

Figure 3:
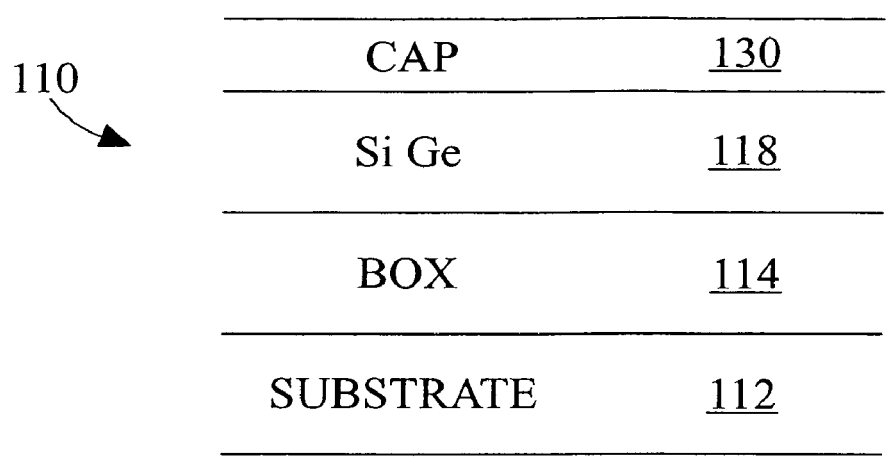
FIG. 3 is a schematic cross-sectional view of the portion of the integrated circuit illustrated in FIG. 2, showing a layer deposition operation.

With reference to FIG. 3, substrate 112, oxide layer 114, a silicon germanium layer 118, and a cap layer of 120 are provided in operation 102 (FIG. 1). Silicon germanium layer 118 can be formed by transfer using wafer bonding technique, and can have any thickness. Cap layer 120 is preferably a layer of silicon dioxide and can be deposited using a deposition technique, such as chemical vapor deposition (CVD). In an exemplary embodiment, silicon germanium layer 118 has a thickness of 30 nm and cap layer 120 has a thickness of 20 nm. Silicon germanium layer 118 can have a concentration of 30% of silicon germanium. Substrate 112 and layer 114 and 118 can be a silicon-on-insulator (SOI) substrate purchased from a wafer manufacturer.

Figure 4:
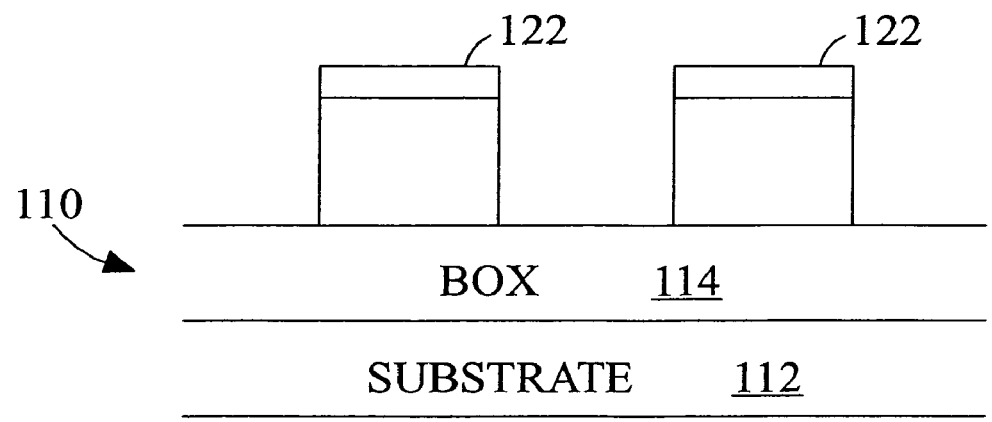
FIG. 4 is a schematic cross-sectional view of the portion of the integrated circuit illustrated in FIG. 2, showing a patterning operation.

In FIG. 4, structures 122 are formed from silicon germanium 118 and cap layer 120 in an operation 104 (FIG. 1) in which silicon germanium layer 118 and cap layer 120 are patterned. In an exemplary embodiment, silicon germanium layer 118 and cap layer 120 are patterned using a process in which a photoresist layer is deposited and patterned. The patterned photoresist layer is then used as a mask to selectively remove portions of the silicon germanium layer 118 and cap layer 120. Remaining portions of the silicon germanium layer 118 and cap layer 120 define structures 122. Other patterning processes may also be utilized in the formation of structures 122. For example, other masking materials can be provided above layer 120.

Figure 5:
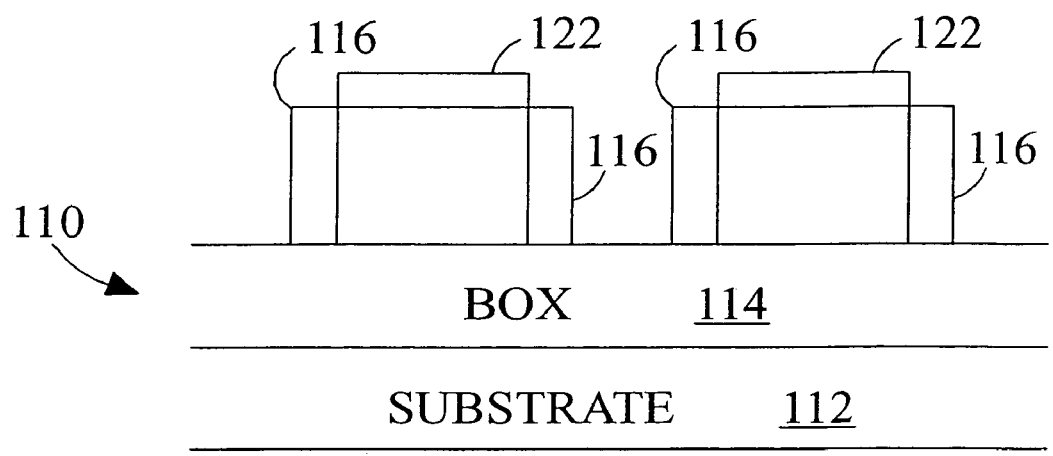
FIG. 5 is a schematic cross-sectional view of the portion of the integrated circuit illustrated in FIG. 2, showing a sidewall formation operation.

In FIG. 5, fins 116 are formed as sidewall structures along lateral side walls of structures 122 in an operation 106 (FIG. 1). As discussed above with respect to FIG. 1, fins are grown using an epitaxial process. The epitaxial process parameters are such that there is no growth occurring on surfacess other than silicon germanium. In combination, fins 116 and structure 122 define a portion of a finFET structure in which fins 116 connect source and drain regions and structures 122 comprise gate structures.

Figure 6:
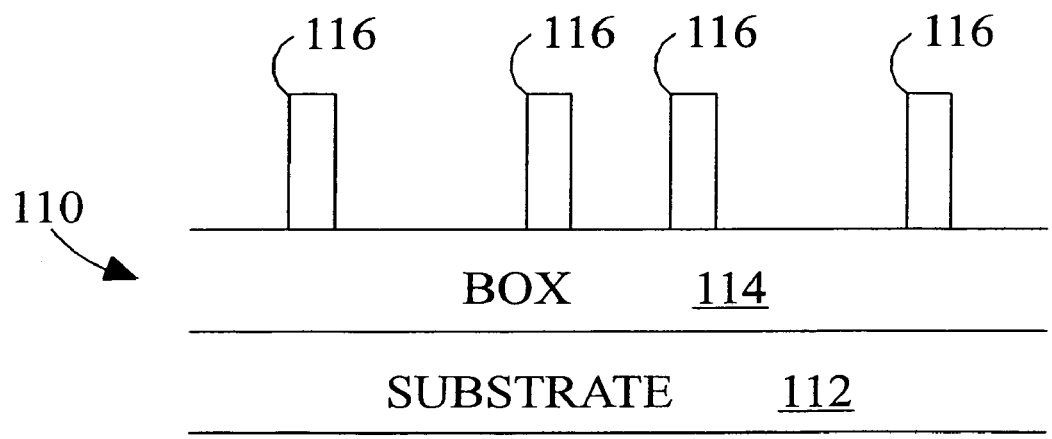
FIG. 6 is a schematic cross-sectional view of the portion of the integrated circuit illustrated in FIG. 2, showing a gate removal operation.

In FIG. 6, structures 122 are removed in an operation 108 (FIG. 1). The removal operation can include the formation of a mask and a selective etch that removes structures 122 and leaves fins 116 unaltered. As such, strainted silicon structures remain and serve to connect device features.

Figure 7:
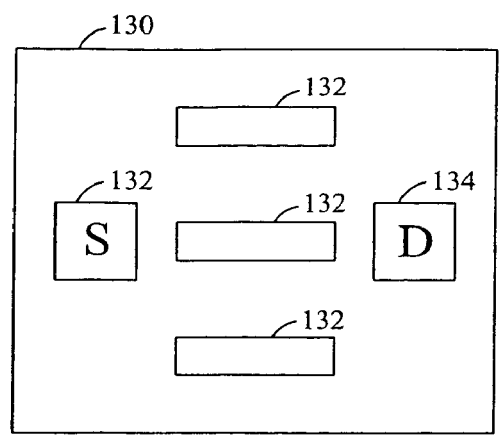
FIG. 7 is a schematic top view of a portion of an integrated circuit including four dummy fins in accordance with another exemplary embodiment.

FIG. 7 illustrates a top view of portion 110 including dummy structures 152 located between a source region 132 and a drain region 134. Source region 132 and drain region 134 are provided in a silicon germanium region 130.

Figure 8:
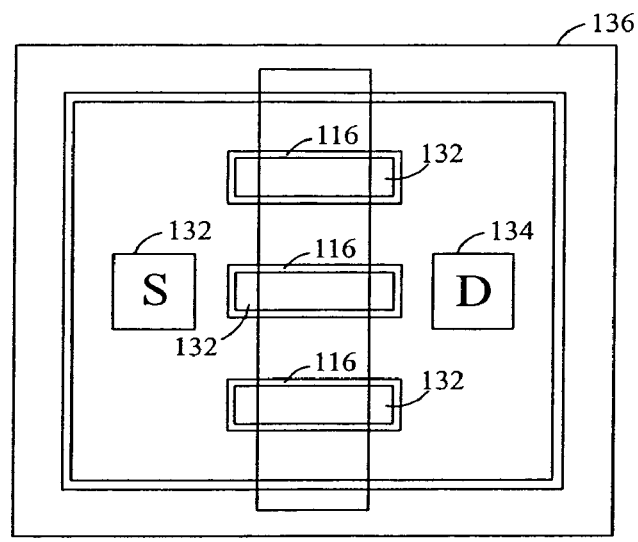
FIG. 8 is a schematic top view of a portion of an integrated circuit including strained silicon epitaxial formation and a mask in accordance with an exemplary embodiment.

In FIG. 8, strained silicon is grown on dummy structures 152 to form fins 116. Also shown is a mask 136 that can be formed to cover source region 132 and drain region 134. Mask 136 provides a window to dummy structures 152 and nearby portions of silicon germanium region 130 such that dummy structures 152 and these portions of silicon germanium region 130 can be removed during a selective etch process.

Figure 9:
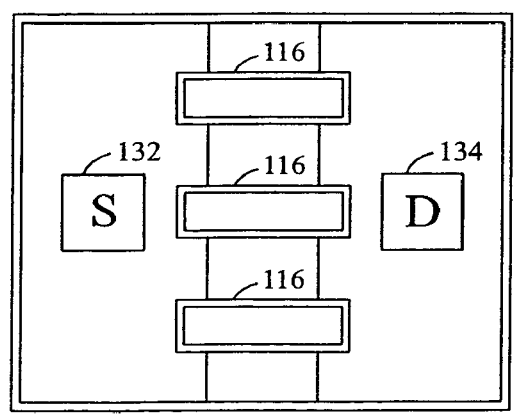
FIG. 9 is a schematic top view of the portion of the integrated circuit shown in FIG. 8 after the dummy fins have been removed leaving eight strained silicon fins.

FIG. 9 illustrates a top view of portion 110 after a selective etching of portions of silicon germanium region 130 and dummy structures 152. Dummy structures 152 are also preferably formed of silicon germanium. Mask 136 is removed after the selective etching process.

Advantageously, strained silicon fins 116 connect source region 132 and drain region 134, providing enhanced mobility for electrons in a transistor by reducing the scattering of electrons. As such, electrons pass from source region 132 to drain region 134 more efficiently.

While the above exemplary embodiments have been described with regard to the formation of a strained silicon finFET using an epitaxial layer, other formation processes can be utilized. Further, system parameters and design criteria can effect the selection of materials and thicknesses without departing from the scope of the invention. The invention is not limited to a particular embodiment, but extends to various modifications, combinations, and permutations that never less fall within the scope and spirit of the appended claims.

What is claimed is:
1. A method of forming a finFET using a sidewall epitaxial layer, the method comprising:
  forming a silicon germanium (SiGe) layer above an oxide layer above a substrate;
  forming a cap layer above the SiGe layer;
  removing portions of the SiGe layer and the cap layer to form a feature;

forming sidewalls along lateral walls of the feature, wherein the sidewalls comprise epitaxially grown strained silicon; and removing the feature.

2. The method of claim 1, wherein the SiGe layer has a thickness of 5–50 nm.

3. The method of claim 1, wherein the feature has a width of 100 nm or more.

4. The method of claim 1, wherein the sidewalls have a width of 1–50 nm.

5. The method of claim 1, further comprising forming a source region and a drain region.

6. The method of claim 5, wherein the source region and drain region are formed in a silicon germanium layer located above the oxide layer.

7. The method of claim 1, wherein the cap layer comprises silicon dioxide.

8. A method of forming structures, the method comprising:

depositing a material layer above an oxide layer above a substrate;

depositing a cap layer above the material layer;

patterning the material layer and the cap layer to form a gate structure;

forming sidewalls along lateral walls of the gate structure, wherein the sidewalls comprise epitaxially grown strained silicon; and providing a selective etch to remove the gate structure and leave the sidewalls to define structures.

9. The method of claim 7, wherein the material layer comprises silicon germanium.

10. The method of claim 7, wherein the sidewalls have a width of 50 nm or less.

11. The method of claim 10, further comprising forming a mask covering the source and drain and exposing the gate structure and at least a portion of the structures.

* * * * *

UNITED STATES PATENT AND TRADEMARK OFFICE
CERTIFICATE OF CORRECTION

| | | |
|---|---|---|
| PATENT NO. | : 7,078,299 B2 | Page 1 of 1 |
| APPLICATION NO. | : 10/654631 | |
| DATED | : July 18, 2006 | |
| INVENTOR(S) | : Witold P. Maszara et al. | |

It is certified that error appears in the above-identified patent and that said Letters Patent is hereby corrected as shown below:

IN THE CLAIMS:

Column 6, Line 11: Delete "claim 7" and replace with --claim 8--.

Column 6, Line 13: Delete "claim 7" and replace with --claim 8--.

Signed and Sealed this

Twenty-seventh Day of March, 2007

JON W. DUDAS
*Director of the United States Patent and Trademark Office*